United States Patent
Labdag et al.

(10) Patent No.: US 8,870,908 B2
(45) Date of Patent: Oct. 28, 2014

(54) TWISTED PRIMARY COIL FOR VASCULAR THERAPY

(75) Inventors: Fatima-Ezzahra Labdag, Palo Alto, CA (US); Jasbir Badesha, Milpitas, CA (US)

(73) Assignee: DePuy Synthes Products, LLC, Raynham, MA (US)

( * ) Notice: Subject to any disclaimer, the term of this patent is extended or adjusted under 35 U.S.C. 154(b) by 1193 days.

(21) Appl. No.: 12/193,602

(22) Filed: Aug. 18, 2008

(65) Prior Publication Data

US 2009/0069836 A1 Mar. 12, 2009

Related U.S. Application Data

(60) Provisional application No. 60/956,509, filed on Aug. 17, 2007.

(51) Int. Cl.
*A61M 29/00* (2006.01)
*A61B 17/12* (2006.01)
*A61B 17/00* (2006.01)

(52) U.S. Cl.
CPC ..... *A61B 17/12022* (2013.01); *A61B 17/12154* (2013.01); *A61B 17/12145* (2013.01); *A61B 2017/00526* (2013.01)
USPC ...................................................... 606/200

(58) Field of Classification Search
USPC ......... 606/108, 191, 194, 198, 200; 623/1.22; 267/166, 180; 170/71 C
See application file for complete search history.

(56) References Cited

U.S. PATENT DOCUMENTS

| | | | | |
|---|---|---|---|---|
| 2,607,582 | A | * | 8/1952 | Jurgens .......................... 267/180 |
| 3,334,629 | A | | 8/1967 | Cohn |
| 3,452,742 | A | | 7/1969 | Muller |
| 3,649,224 | A | | 3/1972 | Anderson et al. |
| 3,868,956 | A | | 3/1975 | Alfidi et al. |
| 4,110,418 | A | * | 8/1978 | Martin .............................. 261/98 |
| 4,494,531 | A | | 1/1985 | Gianturco |
| 4,503,569 | A | | 3/1985 | Dotter |
| 4,512,338 | A | | 4/1985 | Balko et al. |
| 4,553,545 | A | | 11/1985 | Maass et al. |
| 4,638,803 | A | | 1/1987 | Rand |
| 4,655,771 | A | | 4/1987 | Wallsten |
| 4,695,426 | A | | 9/1987 | Nylund |
| 4,718,907 | A | | 1/1988 | Karwoski et al. |
| 4,748,986 | A | | 6/1988 | Morrison et al. |

(Continued)

FOREIGN PATENT DOCUMENTS

DE 32 03 410 A1 11/1982
DE 197 04 269 A1 11/1997

(Continued)

OTHER PUBLICATIONS

International Search Report issued Mar. 17, 2009, pp. 1-3.

(Continued)

*Primary Examiner* — Katherine M Shi

(57) ABSTRACT

A flexible metal wire coil is formed with a twisted coil pattern, by forming a primary coil on a special mandrel formed from two or more strands of material twisted helically about a longitudinal axis to have a helical shape. The primary coil wire is wound around the mandrel to give the primary coil a twisted shape corresponding to the helical shape of the mandrel.

14 Claims, 4 Drawing Sheets

(56) References Cited

U.S. PATENT DOCUMENTS

| | | |
|---|---|---|
| 4,768,507 A | 9/1988 | Fischell et al. |
| 4,795,458 A | 1/1989 | Regan |
| 4,800,882 A | 1/1989 | Gianturco |
| 4,813,925 A | 3/1989 | Anderson, Jr. et al. |
| 4,820,298 A | 4/1989 | Leveen et al. |
| 4,830,003 A | 5/1989 | Wolff et al. |
| 4,850,960 A | 7/1989 | Grayzel |
| 4,856,516 A | 8/1989 | Hillstead |
| 4,950,258 A | 8/1990 | Kawai et al. |
| 4,954,126 A | 9/1990 | Wallsten |
| 4,957,479 A | 9/1990 | Roemer |
| 4,957,501 A | 9/1990 | Lahille et al. |
| 4,990,155 A | 2/1991 | Wilkoff |
| 4,994,069 A | 2/1991 | Ritchart et al. |
| 5,026,377 A | 6/1991 | Burton et al. |
| 5,041,084 A | 8/1991 | DeVries et al. |
| 5,064,435 A | 11/1991 | Porter |
| 5,071,407 A | 12/1991 | Termin et al. |
| 5,104,404 A | 4/1992 | Wolff |
| 5,108,407 A | 4/1992 | Geremia et al. |
| 5,122,136 A | 6/1992 | Guglielmi et al. |
| 5,133,731 A | 7/1992 | Butler et al. |
| 5,133,732 A | 7/1992 | Wiktor |
| 5,139,243 A | 8/1992 | Balsells |
| 5,141,502 A | 8/1992 | Macaluso, Jr. |
| 5,143,085 A | 9/1992 | Wilson |
| 5,147,370 A | 9/1992 | McNamara et al. |
| 5,151,105 A | 9/1992 | Kwan-Gett |
| 5,160,341 A | 11/1992 | Brenneman et al. |
| 5,176,625 A | 1/1993 | Brisson |
| 5,176,661 A | 1/1993 | Evard et al. |
| 5,183,085 A | 2/1993 | Timmermans |
| 5,186,992 A | 2/1993 | Kite, III |
| 1,341,052 A | 4/1993 | Gale |
| 5,203,772 A | 4/1993 | Hammerslag et al. |
| 1,667,730 A | 5/1993 | Green |
| 5,211,183 A | 5/1993 | Wilson |
| 2,078,182 A | 6/1993 | MacFarland |
| 2,549,335 A | 6/1993 | Rahthus |
| 5,217,484 A | 6/1993 | Marks |
| 5,222,969 A | 6/1993 | Gillis |
| 5,226,911 A | 7/1993 | Chee et al. |
| 5,228,453 A | 7/1993 | Sepetka |
| 5,234,437 A | 8/1993 | Sepetka |
| 5,234,456 A | 8/1993 | Silvestrini |
| 5,250,071 A | 10/1993 | Palermo |
| 5,256,146 A | 10/1993 | Ensminger et al. |
| 5,261,916 A | 11/1993 | Engelson |
| 5,269,752 A | 12/1993 | Bennett |
| 5,304,194 A | 4/1994 | Chee et al. |
| 5,304,195 A | 4/1994 | Twyford, Jr. et al. |
| 5,312,356 A | 5/1994 | Engelson et al. |
| 5,312,415 A | 5/1994 | Palermo |
| 5,334,210 A | 8/1994 | Gianturco |
| 5,336,205 A | 8/1994 | Zenzen et al. |
| 5,342,387 A | 8/1994 | Summers |
| 5,350,397 A | 9/1994 | Palermo et al. |
| 5,354,295 A | 10/1994 | Guglielmi et al. |
| 5,380,304 A | 1/1995 | Parker |
| 5,382,259 A | 1/1995 | Phelps et al. |
| 5,417,708 A | 5/1995 | Hall et al. |
| 5,421,338 A | 6/1995 | Crowley et al. |
| 5,437,282 A | 8/1995 | Koger et al. |
| 5,441,516 A | 8/1995 | Wang et al. |
| 5,443,478 A | 8/1995 | Purdy |
| 5,514,176 A | 5/1996 | Bosley, Jr. |
| 5,522,822 A | 6/1996 | Phelps et al. |
| 5,522,836 A | 6/1996 | Palermo |
| 5,527,338 A | 6/1996 | Purdy |
| 5,536,274 A | 7/1996 | Neuss |
| 5,540,680 A | 7/1996 | Guglielmi et al. |
| 5,549,624 A | 8/1996 | Mirigian et al. |
| 5,562,641 A | 10/1996 | Flomenblit et al. |
| 5,562,698 A | 10/1996 | Parker |
| 5,569,245 A | 10/1996 | Guglielmi et al. |
| 5,582,619 A | 12/1996 | Ken |
| 5,601,600 A | 2/1997 | Ton |
| 5,607,445 A | 3/1997 | Summers |
| 5,624,449 A | 4/1997 | Pham et al. |
| 5,624,461 A | 4/1997 | Mariant |
| 5,637,113 A | 6/1997 | Tartaglia et al. |
| 5,639,277 A | 6/1997 | Mariant et al. |
| 5,643,254 A | 7/1997 | Scheldrup et al. |
| 5,645,082 A | 7/1997 | Sung et al. |
| 5,645,558 A | 7/1997 | Horton |
| 5,649,949 A | 7/1997 | Wallace et al. |
| 5,667,522 A | 9/1997 | Flomenblit et al. |
| 5,669,905 A | 9/1997 | Scheldrup et al. |
| 5,669,931 A | 9/1997 | Kupiecki et al. |
| 5,676,697 A | 10/1997 | McDonald |
| 5,690,643 A | 11/1997 | Wijay |
| 5,690,666 A | 11/1997 | Berenstein et al. |
| 5,690,667 A | 11/1997 | Gia |
| 5,690,671 A | 11/1997 | McGurk et al. |
| 5,693,067 A | 12/1997 | Purdy |
| 5,697,948 A | 12/1997 | Marin et al. |
| 5,700,258 A | 12/1997 | Mirigian et al. |
| 5,718,711 A | 2/1998 | Berenstein et al. |
| 5,725,546 A | 3/1998 | Samson |
| 5,733,329 A | 3/1998 | Wallace et al. |
| 5,743,905 A | 4/1998 | Eder et al. |
| 5,746,769 A | 5/1998 | Ton et al. |
| 5,749,891 A | 5/1998 | Ken et al. |
| 5,749,894 A | 5/1998 | Engelson |
| 5,766,160 A | 6/1998 | Samson et al. |
| 5,800,453 A | 9/1998 | Gia |
| 5,800,455 A | 9/1998 | Palermo et al. |
| 5,800,520 A | 9/1998 | Fogarty et al. |
| 5,807,404 A | 9/1998 | Richter |
| 5,824,037 A | 10/1998 | Fogarty et al. |
| 5,830,230 A | 11/1998 | Berryman et al. |
| 5,843,118 A | 12/1998 | Sepetka et al. |
| 5,944,733 A | 8/1999 | Engelson |
| 6,013,084 A | 1/2000 | Ken et al. |
| 6,544,275 B1 * | 4/2003 | Teoh ............................ 606/158 |
| 7,055,812 B2 * | 6/2006 | Balsells ....................... 267/167 |
| 2002/0026234 A1 * | 2/2002 | Li et al. ....................... 623/1.34 |
| 2005/0267511 A1 * | 12/2005 | Marks et al. .................. 606/200 |
| 2006/0200190 A1 * | 9/2006 | Lorenzo et al. ............... 606/200 |

FOREIGN PATENT DOCUMENTS

| | | |
|---|---|---|
| EP | 0 183372 A1 | 6/1986 |
| EP | 0 382014 A1 | 8/1990 |
| EP | 0 747 012 A1 | 12/1996 |
| EP | 0 747 014 A1 | 12/1996 |
| EP | 0 820 726 A2 | 1/1998 |
| GB | 2 066 839 A | 7/1981 |
| WO | 94/10936 | 5/1994 |
| WO | 94/16629 | 8/1994 |
| WO | 95/18585 | 7/1995 |
| WO | 97/48351 | 12/1997 |
| WO | 99/07294 | 2/1999 |
| WO | 99/29260 | 6/1999 |
| WO | 01/45571 A1 | 6/2001 |

OTHER PUBLICATIONS

"Dictionary of Matallurgy" by Birchon, p. 182, 1965.

Y. Pierre Gobin, M.D. et al., "Treatment of Large and Giant Fusiform Intracranial Aneurysms with Guglielmi Detachable Coils," J. Neurosurg., Jan. 1996, pp. 55-62, vol. 84.

Cameron G. McDougall, M.D., et al., "Endovascular Treatment of Basilar Tip Aneurysms using Electrolytically Detachable Coils," J. Neurosurg., Mar. 1996, pp. 393-399, vol. 84.

Sadek K. Hilal, M.D. et al., Journal of Neurological Surgery "Therapeutic Percutaneous Embolization for Extra-Axial Vascular Lesions of the Head, Neck and Spine" Sp., 1975; pp. 275-287.

Stephen L. Kaufman, M.D. et al., Investigative Radiology, May-Jun. 1978 "Transcatheter Embolization with Microfibrillar Collagen in Swine"; pp. 200-204.

Ashok J. Kumar, et al., Journal of Neuroradiology (1982) "Preoperative Embolization of Hypervascular Head and Neck Neoplasms Using Microfibrillar, Collagen", pp. 163-168.

(56) References Cited

OTHER PUBLICATIONS

Richard E. Latchaw, M.D. et al., Radiology (1979)" Polyvinyl Foam Embolization of Vascular and Neoplastic Lesions of the Head, Neck and Spine" pp. 669-679.
Stewart R. Reuter, M.D. et al. American Journal of Radiology, Sep. 1975 "Selective Arterial Embolization for Control of Massive Upper Gastrointestinal Bleeding" pp. 119-126.
Glenn H. Roberson, et al., American Journal of Radiology, Oct. 1979 "Therapeutic Embolization of Juvenile Angiofibroma" pp. 657-663.
Sidney Wallace, M.D. et al., Cancer, Oct. 1979 "Arterial Occlusion of Pelvic Bone Tumors"; pp. 322-325 & 661-663.
Mechanical Device for Arterial Occlusion by C. Gianturco, M.D. et al., Jul. pp. 428-435.
"Therapeutic Vascular Occlusion Utilizing Steel Coil Technique: Clinical Applications" by Sidney Wallace, et al., AmJ. Roentgenol (1976); pp. 381-387.
"Transcatheter Intravascular Coil Occulusion of Experimental Arteriovenous Fistulas", by James H. Anderson, et al., Am. J. Roentgenol, Nov. 1977, pp. 795-798.
"Mini' Gianturco Stainless Steel Coils for Transcatheter Vascular Occlusion" James H. Anderson, et al., From the Department of Diagnostic Radiology at the University of Texas System Cancer Center, Aug. 1978, pp. 301-303.
"A New Improved Coil for Tapered-Tip Catheter for Arterial Occlusion" By Vince P. Chuang, M.D., et al. May 1980, pp. 507-509.
"Neurosurgery Interactive Article Part 2—Clinical Studies Embolization of Cerebral Arteriovenous Malformations: Part II—Aspects of Complications and Late Outcome" by Christer Lunqvist, M.D.Ph.D., et al. Sep. 1996, pp. 1-16.
"Shape Memory Alloys" by Jeff Perkins, pp. 1095-1096.
Christos A. Athanasoulis, M.D. The New England Journal of Medicine, May 22, 1980 "Therapeutic Applications of Angiography" pp. 1174-1179 (2 of 2).
Christos A. Athanasoulis, M.D. The New England Journal of Medicine, May 15, 1980 "Therapeutic Applications of Angiography" pp. 1117-1125 (1 of 2).
Alex Berestein, M.D. And Irvin I. Kricheff, M.D. "Catheter and Material Selection for Transarterial Embolization: Technical Considerations" Radiology, Sep. 1979, pp. 631-639.
O.A. Battista, et al. Journal of Applied Polymer Science 1967 "Colloidal Macromolecular Phenomena. Part. II. Novel Microcrystals of Polymers" pp. 481-498.

* cited by examiner

TWISTED PRIMARY COIL FOR VASCULAR THERAPY

CROSS-REFERENCES TO RELATED APPLICATIONS

This application is based on Provisional Application No. 60/956,509 filed 17 Aug. 2007.

BACKGROUND OF THE INVENTION

1. Field of the Invention

This invention relates generally to implantable devices for vascular interventional therapeutic treatment or vascular surgery, and more particularly concerns a coil with a twisted pattern that exhibits improved flexibility and/or secondary coil shape capabilities along the length of the coil, said coil being particularly useful as a primary coil for more complex shapes used in various vascular interventional therapies.

2. Description of the Related Art

Vasoocclusive devices can take a variety of configurations, and are generally formed of one or more elements that are larger in the deployed configuration than when they are within a delivery catheter prior to placement. One widely used vasoocclusive device is a helical wire coil having a secondary deployed configuration which may be dimensioned to obstruct all or a portion of a particular part of the vasculature of interest. One anatomically shaped vasoocclusive device is known that forms itself into a shape of an anatomical cavity such as an aneurysm and is made of a pre-formed primary coil of flexible material such as a platinum alloy.

The vasoocclusive members can be sized and shaped so that in their deployed configuration they fit within a vascular cavity or vesicle such as for treatment of an aneurysm or fistula. The vasoocclusive member can be first helically wound in a generally linear fashion and is then wound around a mandrel or form shaped to conform with the secondary shape desired, and heat treated to retain the basic shape of the mandrel after removal from the heated form.

A variable stiffness coil that will deform more readily along certain predetermined sections of the coil can be useful for filling aneurysms of various sizes and shapes. A variable cross section conical vasoocclusive coil is known that can achieve variations in stiffness of the coil by variation of the diameter in different regions of the coil or variations in the composition of the coil.

A known method of forming a primary wind coil is to wind a continuous coil of a metal wire such as a platinum wire, for example, on a cylindrical wire mandrel, typically about 0.010 inch in diameter. The resulting primary wind coil typically has the same bending stiffness in all directions because it is formed as a helix about a constant diameter cylindrical mandrel, so that the coil has a constant bending moment about the longitudinal axis of the coil in all planes along the longitudinal axis of the coil.

It would be desirable to provide a flexible metal wire coil for use as a structural element to form a densely packed therapeutic vasoocclusive coil, or clot remover, for example, that allows for the coil to be flexible prior to deployment and to more completely fill and occupy a given space, while retaining the softness of a smaller coil and that can make the delivery of the coil easier. It would also be desirable to provide a primary wind coil that does not have a specific relaxed shape so that it can more completely fill an area to be treated than primary wind coils which are currently available. The present invention meets these and other needs.

SUMMARY OF THE INVENTION

Briefly, and in general terms, the present invention provides for a flexible metal wire coil that exhibits better packing density in aneurysms or the like than conventional primary coils, the coil of the invention having a twisted coil pattern, a method of forming the coil, a mandrel for forming the coil, and a method for forming the mandrel.

In a first currently preferred embodiment, the present invention provides for a densely packing primary wind coil with a non-circular cross-sectional shape that is elongated along at least one axis transverse to the longitudinal axis of the coil, with the at least one transverse axis rotating along the longitudinal axis, to provide the primary wind coil with at least one bending moment that precesses along the longitudinal axis. The cross-sectional shape of the primary wind coil may be oval, oblong, triangular, or some other geometric shape, for example. In another presently preferred aspect, the primary wind coil is formed from a flexible elongated strand of material such as a metal or metal alloy. In a currently preferred embodiment the metal is a platinum alloy. The flexible elongated strand of material may have a diameter of approximately 0.0015 to 0.002 inch, for example. The primary wind coil can be further formed to have a secondary shape, such as a spherical, spheroidal, conical, or cylindrical secondary shape, for example, or a combination of such shapes. In another presently preferred aspect, the at least one precessing transverse axis of the primary wind coil provides the primary wind coil with at least one precessing bending moment, so that the plane of minimum bending force of the primary wind coil varies along the length of the primary wind coil, allowing the deployed shape of the coil to be a highly densely packed configuration, with a higher percentage of filling and a higher density of packing compared with coils with symmetric cross sections, when the coil is used as a therapeutic vasoocclusive coil, clot remover, or other therapeutic device. In another aspect, the primary wind coil defines an interior space, and an axial element may be disposed in the interior space of the primary wind coil to increase stretch resistance the additional element extending along the longitudinal axis of the primary wind coil, so that the primary wind coil may be used as a retractable clot remover. The axial element may be formed of stretch resistant plastic thread or a metal such as nitinol, for example, and also may be configured to have a secondary shape in its relaxed state.

In the method of forming a mandrel for use in making a vasoocclusive coil according to the invention, the mandrel is formed to have a non-circular cross-sectional shape that is elongated along at least one axis that is transverse to the longitudinal axis, with the at least one transverse axis precessing along the longitudinal axis, that is to say rotating about the longitudinal axis as it progresses along that axis. In one presently preferred construction of a mandrel, two or more parallel strands of wire may be twisted helically about a longitudinal axis to provide a multi-helical mandrel having a external surface with a multi-helical shape. In a presently preferred aspect, the step of twisting two or more parallel strands of material involves twisting parallel strands of material about the longitudinal axis, so as to form the mandrel in the shape of a double helix. Similarly, three or more strands can be twisted along the longitudinal axis to create a mandrel with triangular, square, or other cross sections. In another aspect, the plurality of strands of material that are twisted to form the mandrel are formed of metal wire, such as a spring wire, typically a stainless steel wire, for example, although other similar metal or polymeric materials may also be suitable. The plurality of strands of material may have a diameter of approximately 0.0035 to approximately 0.055 inch, so that the mandrel may have a diameter of approximately 0.0070 inch to approximately 0.11 inch. In another aspect of the invention, the mandrel may be constructed of a single wire with a desired non-circular cross section, the wire mandrel then twisted about its longitudinal axis to form the final desired shape of the mandrel. Similarly, the mandrel can be found with a variable longitudinal pitch to create a primary coil with variable binding moment in some portions of the coil compared to others.

In one presently preferred method of forming the vasoocclusive coil according to the invention, a flexible metal wire is wound around a length of the mandrel to form the primary wind coil having a twisted shape corresponding to the multi-helical shape of the external surface of the mandrel. In another aspect, an axial member may also be inserted into the interior space of the primary wind coil along the longitudinal axis of the primary wind coil, to provide stretch resistance or to facilitate the use of the primary wind coil as a clot remover.

The present invention provides for a structure, method of manufacture, and manufacturing mandrel for the creation of coils that can be tailored to provide a wide variety of characteristics which are desirable for the occlusion of body cavities, including greater filling of the cavity and better behavior in forming secondary shapes, including "random breaks" in the formation of secondary shapes to more easily accommodate non-uniform aneurysms and the like. These and other aspects and advantages of the invention will become apparent from the following detailed description and the accompanying drawings which illustrate by way of example the features of the invention.

DETAILED DESCRIPTION OF THE PREFERRED EMBODIMENTS

Figure 1A:
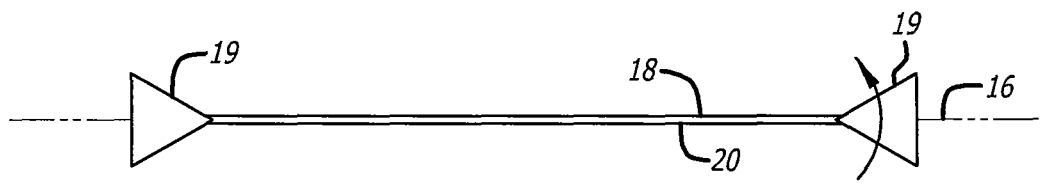
FIG. 1A is a schematic diagram illustrating the placement and twisting of a pair of parallel core strands in a spindle in preparation for making one form of a twisted mandrel for forming a primary wind coil having a twisted shape according to the present invention.
Figure 1B:
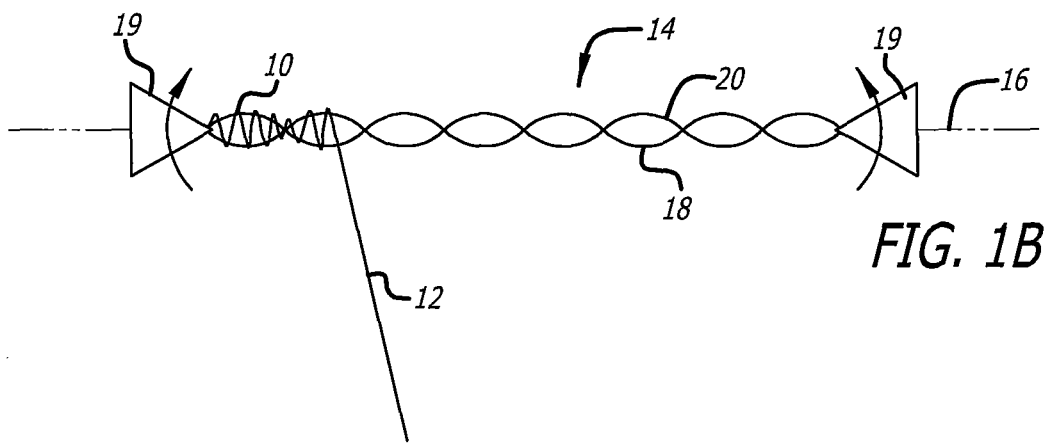
FIG. 1B is a schematic diagram illustrating winding of a flexible metal coil wire around a length of the twisted mandrel having a double helical shape of to form a primary wind coil having a twisted shape with a transverse axis precessing along the longitudinal axis according to the present invention.
Figure 2:
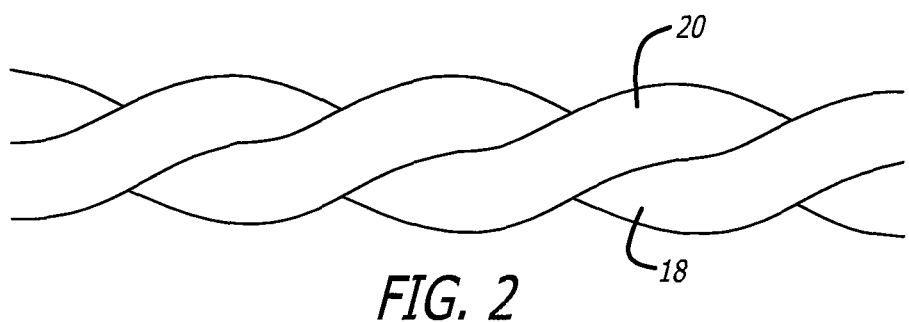
FIG. 2 is an enlarged view of a length of the twisted mandrel having a double helical shape of FIG. 1B.

As is illustrated in the drawings, which are provided by way of illustration and not by way of limitation, the present invention provides for a primary wind flexible metal wire coil 10 having a twisted coil pattern, illustrated in FIGS. 1B, 3A, and 12-15. Referring to FIGS. 1A and 1B, according to the method of the invention, the twisted coil pattern may be imparted to the primary wind coil by winding an elongated strand of flexible material, such as a flexible wire 12, formed of metal or metal alloy, for example, over an elongated multi-helical or twisted mandrel 14 having a central longitudinal axis 16. In one presently preferred form illustrated in FIG. 1A, the elongated multi-helical or twisted mandrel may be formed from a plurality of parallel core strands, such as a pair of parallel core strands of material 18, 20, that have been wrapped or twisted helically about the longitudinal axis of the mandrel, thereby giving the mandrel a multi-helical shape, such as a double helix, as illustrated in FIGS. 1B and 2, i.e., when the mandrel is formed as a twisted helix or spiral from two parallel core strands twisted about around the longitudinal axis of the mandrel. As is shown in FIGS. 1A and 1B, the opposing ends of the parallel core strands 18 and 20 can be secured to opposing chucks 19 of a spindle and twisted to a provide the mandrel with a desired twist cycle pitch.

The mandrel core strands of material that are twisted together are typically round metal wire, such as stainless steel spring wire, although the mandrel core strands may also be made of polymeric material, such as polyethylene, for example. The multi-helical shaped, twisted mandrel may be pre-formed from a twisted pair of parallel round core strands, each as small as approximately 0.0035 to 0.005 inch in diameter, resulting in a mandrel approximately 0.007 to 0.010 inch in diameter, or as large as approximately 0.055 inch in diameter, resulting in a mandrel approximately 0.11 inch in diameter, for example.

Figure 3A:
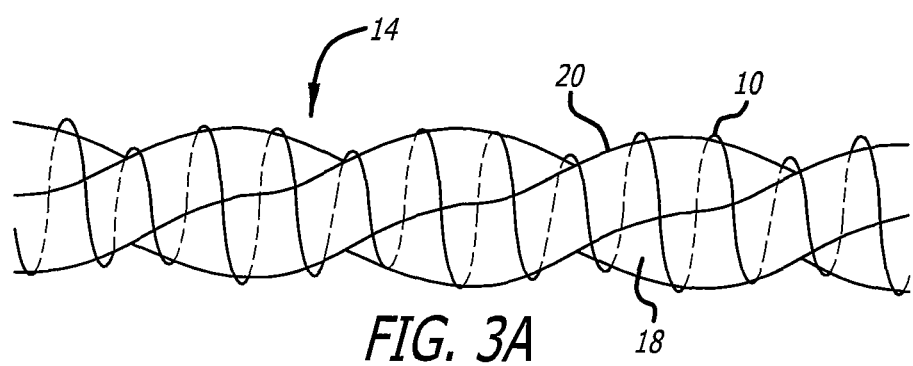
FIG. 3A is a schematic diagram illustrating a side elevational view of a length of a primary wind coil shown wound about a twisted mandrel having a double helical shape of FIG. 1B, shown widely spaced for purposes of illustration, for imparting a twisted pattern with one transverse axis precessing along the longitudinal axis to the coil according to the present invention.
Figure 3B:
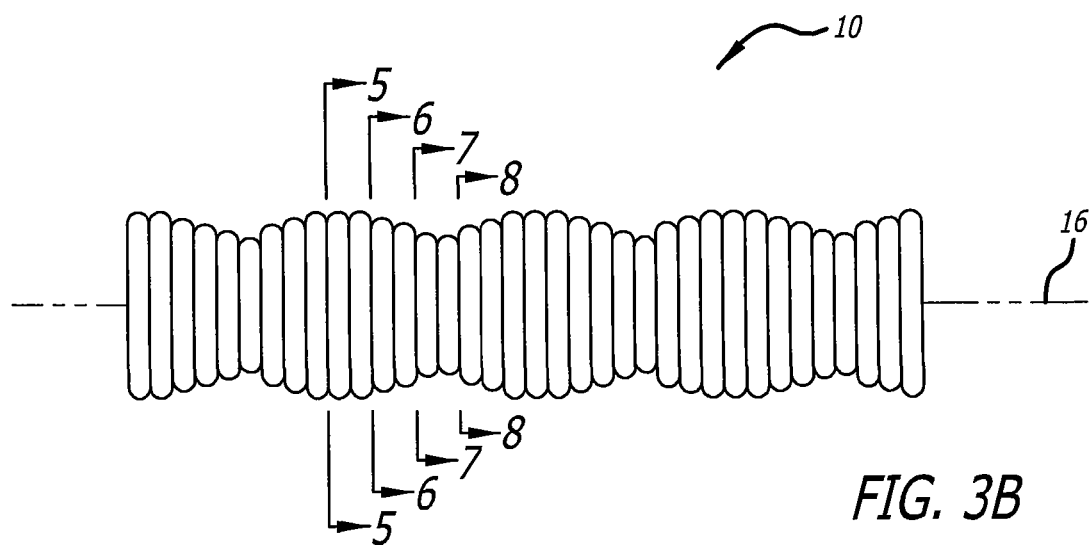
FIG. 3B is a side elevational view of a length of a tightly wound primary wind coil shown wound about the twisted mandrel, with the mandrel removed, and having a twisted pattern elongated along one transverse axis that precesses along the longitudinal axis imparted to the coil by the mandrel according to the present invention.

A primary wind of a coil may be formed on the twisted mandrel by winding a flexible elongated strand of material such as a platinum wire, or platinum alloy, such as platinum-tungsten. For example, the primary wind coil may be formed by a platinum-tungsten alloy (PT-W) wire having an outer diameter of approximately 0.0015 to 0.002 inch, or a platinum wire having an outer diameter of approximately 0.0015 to 0.002 inch, for example, wound around a length of the twisted mandrel, typically with about 500 turns of the flexible metal wire per inch longitudinally along the mandrel. Winding such an elongated flexible strand about such a multi-helical twisted mandrel results in a primary wind coil with a generally twisted shape or pattern corresponding to that of the multi-helical shape of the twisted mandrel, illustrated in FIG. 3B. As is illustrated in FIGS. 5-8, the resulting primary wind coil has a non-circular cross-sectional shape that is elongated along a transverse axis 21 that is transverse to the longitudinal axis. The transverse axis precesses along the longitudinal axis, to provide the primary wind coil with a related bending moment that also precesses about the longitudinal axis. The cross-sectional shape of the primary wind coil formed in this manner may be oval or oblong, for example. The twisted shape or pattern of the primary wind coil thus advantageously provides the primary wind coil with a variable bending moment, herein defined as the plane of minimum bending force, which thus varies in different directions or planes along the primary wind coil.

While not illustrated, it will be understood by those skilled in the art that the mandrel may also be formed by an oval, triangular, or other cross-sectional wire that is twisted about its longitudinal axis to provide the characteristics described herein for mandrels formed entirely by circular cross-sectional wires.

Figure 4:
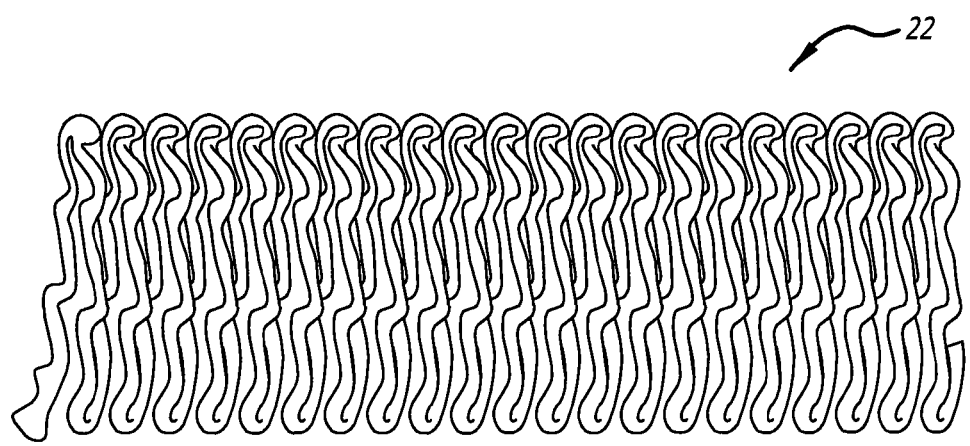
FIG. 4 is a side elevational view of a primary wind coil formed to have a twisted shape formed into a cylindrical secondary shape.
Figure 5:
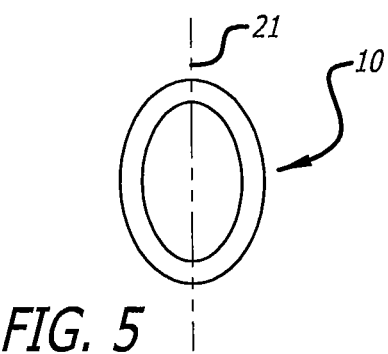
FIG. 5 is a cross-sectional view taken along line 5-5 of FIG. 3B illustrating the precessing of the transverse axis of the primary wind coil along the longitudinal axis.
Figure 6:
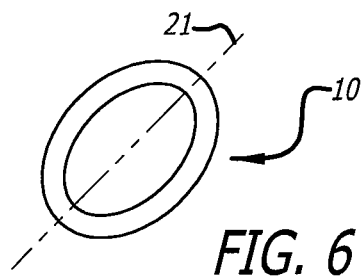
FIG. 6 is a cross-sectional view taken along line 6-6 of FIG. 3B illustrating the precessing of the transverse axis of the primary wind coil along the longitudinal axis.
Figure 7:
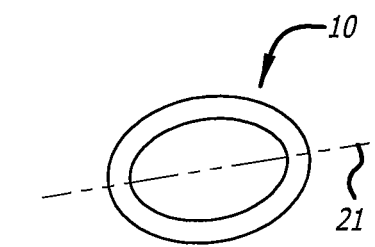
FIG. 7 is a cross-sectional view taken along line 7-7 of FIG. 3B illustrating the precessing of the transverse axis of the primary wind coil along the longitudinal axis.
Figure 8:
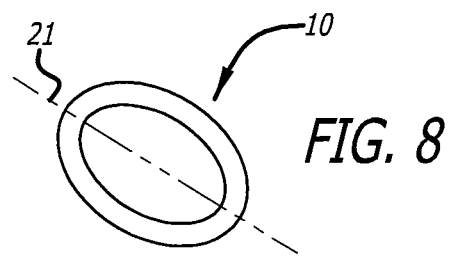
FIG. 8 is a cross-sectional view taken along line 8-8 of FIG. 3B illustrating the precessing of the transverse axis of the primary wind coil along the longitudinal axis.
Figure 9:
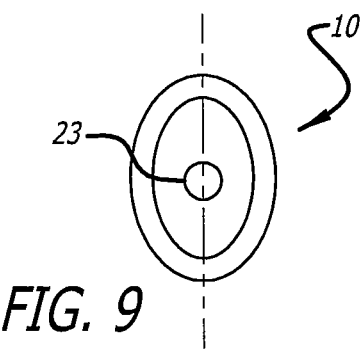
FIG. 9 is a cross-sectional view similar to that of FIG. 5, showing an elongated strand of material inserted into the inner lumen of the primary wind coil.

As is illustrated in FIG. 4, a coil with a secondary shape 22, such as a cylindrical secondary shape, for example, may be formed by winding the primary wind coil about an appropriate cylindrical mandrel (not shown), for example, and setting the cylindrical shape of the cylindrical mandrel in the coil using heat. Alternatively, as is illustrated in illustrated in FIGS. 10 and 11, the secondary shape may be a spherical or spheroidal secondary shape that may be formed by winding the primary wind coil about an appropriate spherical or spheroidal mandrel (not shown), and setting the secondary spherical shape from the spherical or spheroidal mandrel in the coil using heat. In addition, as is illustrated in FIG. 9, an elongated strand of material 23, such as a shaped or non-shaped wire, such as a nitinol wire for example, or a stretch resistant member formed of polymeric material such as polyglycolic acid or polypropylene, for example, may be inserted into the inner lumen of the of the generally tubular shaped primary wind coil, to reinforce the primary wind coil to provide greater stretch resistance to the coil or to allow the primary wind coil to be used as a retractable clot remover, for example.

Exemplary dimensions of a coil with a secondary cylindrical shape are provided in the table below:

| Outer Diameter (mm) | Length (cm) |
|---|---|
| 6 | 26 |
| 7 | 30 |
| 8 | 29 |

Figure 10:
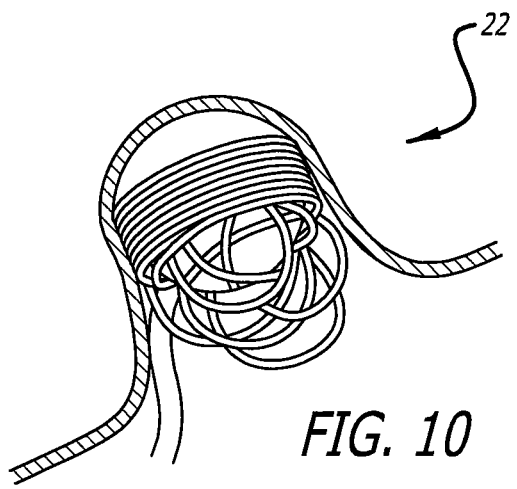
FIG. 10 is a side elevational view of a conventional primary wind coil inserted to fill a generally spherical secondary shaped model of an aneurysm.
Figure 11:
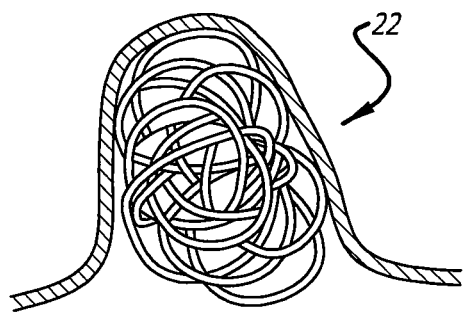
FIG. 11 is a side elevational view of a primary wind coil formed to have a twisted longitudinal shape inserted to fill a generally spherical secondary shape model of an aneurysm, illustrating the greater filling of the aneurysm with the coil of the invention.
Figure 12:
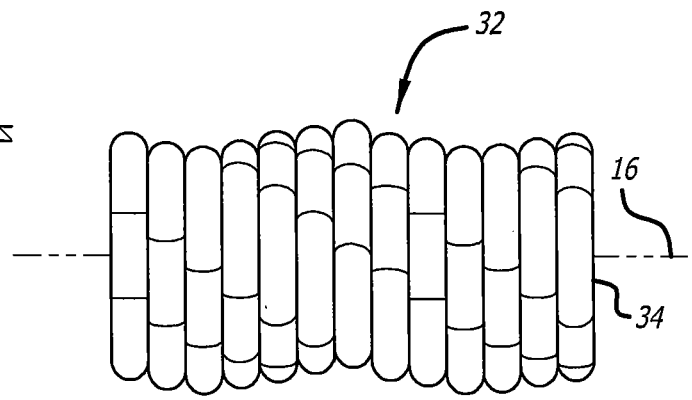
FIG. 12 is a side elevational view of a length of a tightly wound primary wind coil having a twisted shape elongated along two transverse axes that precess along the longitudinal axis according to the present invention according to the present invention.

Referring now to FIG. 10, the figure illustrates the filling of an exemplary aneurysm formed in glass when a symmetrical primary coil without a secondary shape is used to fill the aneurysm. As can be seen from the illustration, the symmetry of the primary coil about its longitudinal axis results in the coil forming layers within the aneurysm resulting in voids in the filling of the aneurysm. FIG. 11 illustrates the improved fill ratio of the same type of aneurysm model when the coil of the present invention is used. The coil of the invention has a "random break" characteristic due to the precession of the bending moment along the longitudinal axis of the coil which results in a greater "fill ratio" of the aneurysm. This characteristic also allows greater flexibility in the treatment of aneurysms or other body cavities with irregular shapes while still being able to accomplish treatment with a single type of coil.

Referring to FIGS. 12-15, a twisted coil pattern may be imparted to a primary wind coil 32 by joining a series of a plurality of generally triangular rings 33 with rounded corners formed of an elongated strand of flexible material 34, or by winding an elongated strand of flexible material 34, such as a flexible wire, formed of metal or metal alloy, such as a platinum wire, or platinum alloy, such as platinum-tungsten, for example, over an elongated multi-helical or twisted mandrel having a central longitudinal axis 16 to provide the primary wind coil with a twisted shape with a generally triangular cross-sectional shape and rounded corners that precesses along the longitudinal axis and a desired twist cycle pitch. For example, the primary wind coil may be formed by a platinum-tungsten alloy (PT-W) wire having an outer diameter of approximately 0.0015 to 0.002 inch, or a platinum wire having an outer diameter of approximately 0.0015 to 0.002 inch, for example, wound around a length of the twisted mandrel, typically with about 20 turns of the flexible metal wire per inch longitudinally along the mandrel. The primary wind coil may, for example, have a twist cycle pitch of about 8 to 9 winds per cycle, for a wire for a wire with a diameter of about 0.0015 inch wrapped with a pitch of about 0.0016 inch, an angle of rotation of about 13-14 degrees.

Figure 13:
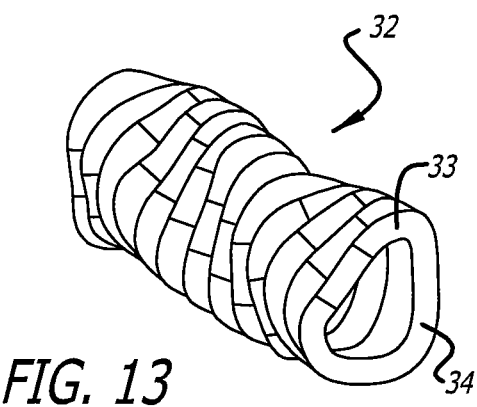
FIG. 13 is a perspective view of the primary wind coil of FIG. 12 having a twisted shape elongated along two transverse axes that precess along the longitudinal axis according to the present invention.
Figure 14:
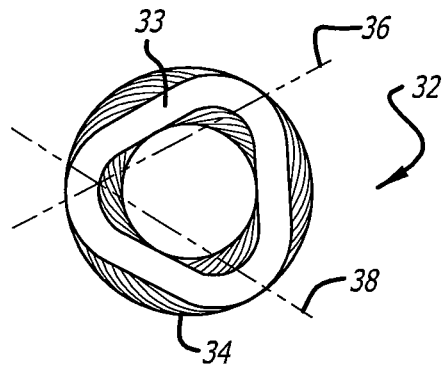
FIG. 14 is an end view of the primary wind coil of FIG. 12 having a twisted shape illustrating the two transverse axes that precess along the longitudinal axis according to the present invention.
Figure 15:
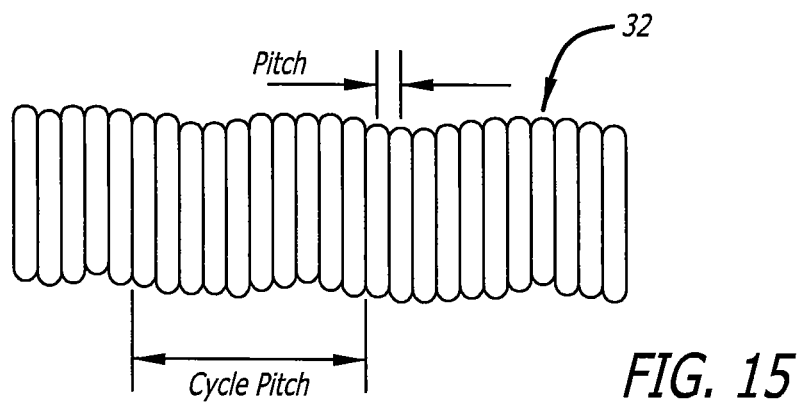
FIG. 15 is a side elevational view of a length of a tightly wound primary wind coil having a twisted shape elongated along two transverse axes that precess along the longitudinal axis similar to FIG. 12, illustrating the one wind pitch and cycle pitch of the primary wind coil.

As is illustrated in FIGS. 13-14, a primary wind coil according to a presently preferred embodiment has a cross-sectional non-circular shape that is elongated along transverse axes (36, 38 as examples) that are at an angle to the longitudinal axis of the primary wind coil. The transverse axes precess along the longitudinal axis, to provide a primary wind coil with two related bending moments (one more resistant to bending than the other due to the non-symmetry with the longitudinal axis) that also precess about the longitudinal axis. The cross-sectional shape of the primary wind coil formed in this manner is generally triangular, with rounded corners, for example. The twisted shape or pattern of the primary wind coil thus advantageously provides the primary wind coil with two bending moments that vary in different directions or planes along the primary wind coil.

As described above, the primary wind coil may be formed into a coil with a secondary shape, such as a cylindrical, conical, spherical, or spheroidal secondary shape, or combinations thereof, for example, and an elongated strand of material, such as a shaped or non-shaped wire, such as a nitinol wire for example, or a stretch resistant member formed of polymeric material such as polyglycolic acid or polypropylene, for example, may be inserted into the inner lumen of the of the generally tubular shaped primary wind coil, to reinforce the primary wind coil, aid stretch resistance of the coil, or allow the primary wind coil to be used as a retractable stent or a clot remover, for example.

While it will be apparent from the foregoing that while particular forms of the invention have been illustrated and described, various modifications can be made without departing from the spirit and scope of the invention. Accordingly, it is not intended that the invention be limited, except as by the appended claims.

The invention claimed is:

1. A primary wind coil, comprising:
a flexible metal wire coiled about a primary wind coil longitudinal axis to form a primary wind coil having an inner lumen, said primary wind coil being elongated along said primary wind coil longitudinal axis, said primary wind coil having an exterior non-circular primary wind coil cross-sectional shape and a corresponding interior non-circular primary wind coil cross-sectional shape, said exterior and corresponding interior non-circular primary wind coil cross-sectional shapes being elongated along a first transverse axis that is transverse to said primary wind coil longitudinal axis, said first transverse axis of said non circular primary wind coil cross sectional shape and said interior non-circular primary wind coil cross-sectional shape precessing along said primary wind coil longitudinal axis to form a repeating twisted coil pattern, said primary wind coil having a first plane of minimum bending force that correspondingly precesses together with said first transverse axis and said interior non-circular primary wind coil cross-sectional shape along said primary wind coil longitudinal axis, wherein said primary wind coil is sized to fit within an aneurysm, fistula or vascular cavity.

2. The primary wind coil of claim 1, wherein said primary wind coil has an external shape and a corresponding internal shape of a double helix.

3. The primary wind coil of claim 1, wherein said exterior and corresponding interior non-circular primary wind coil cross-sectional shapes are selected from the group consisting of oval, oblong and generally triangular with rounded cornered shapes.

4. The primary wind coil of claim 1, wherein said exterior and corresponding interior non-circular primary wind coil cross-sectional shapes are elongated along a second transverse axis that is transverse to said longitudinal axis, said second transverse axis precessing along said primary wind coil longitudinal axis, said primary wind coil having a second plane of minimum bending force that correspondingly precesses along said primary wind coil longitudinal axis.

5. The primary wind coil of claim 4, wherein said primary wind coil is formed to have a secondary shape selected from the group consisting of cylindrical, conical, spherical and spheroidal shapes and combinations thereof.

6. The primary wind coil of claim 1, wherein said primary wind coil has an interior space along a longitudinal axis of the primary wind coil, and further comprising an axial strand of material extending through the interior space along the longitudinal axis of the primary wind coil.

7. The primary wind coil of claim 1, wherein said primary wind coil has a variable bending moment in different planes of the primary wind coil, such that the plane of minimum bending force varies along the length of the primary wind coil.

8. A primary wind coil, comprising:
a flexible metal wire having a wire cross-sectional shape, said flexible metal wire being coiled about a primary wind coil longitudinal axis to form a primary wind coil having an inner lumen with an interior non-circular cross-sectional shape, said primary wind coil being elongated along said primary wind coil longitudinal axis and having an exterior non-circular cross-sectional shape corresponding to said interior non-circular cross-sectional shape, said interior and corresponding exterior non-circular cross-sectional shapes being elongated along a first transverse axis that is transverse to said primary wind coil longitudinal axis and elongated along a second transverse axis that is transverse to said primary wind coil longitudinal axis, said first transverse axis and said second transverse axis of said interior non-circular cross-sectional shape precessing along said primary wind coil longitudinal axis to form a repeating twisted coil pattern, said primary wind coil having first and second planes of minimum bending force that correspondingly precess along said primary wind coil longitudinal axis wherein said non-circular primary wind coil has a first bending resistance along said first transverse axis, and a second bending resistance along said second transverse axis that is greater than said first bending resistance, wherein said primary wind coil is sized to fit within an aneurysm, fistula or vascular cavity.

9. A secondary wind coil, comprising:
a flexible metal wire coiled about a primary wind coil longitudinal axis to form a primary wind coil having an inner lumen, said primary wind coil being elongated along said primary wind coil longitudinal axis and having an exterior non-circular primary wind coil cross-sectional shape and a corresponding interior non-circular primary wind coil cross-sectional shape, said exterior and interior non-circular primary wind coil cross-sectional shapes being elongated along a transverse axis that is transverse to said primary wind coil longitudinal axis, wherein said non-circular primary wind coil has a bending resistance along said transverse axis, said transverse axis and said interior non-circular primary wind coil cross-sectional shape precessing along said primary wind coil longitudinal axis to form a repeating twisted coil pattern, and said primary wind coil having a plane of minimum bending force that correspondingly precesses along said primary wind coil longitudinal axis, wherein said primary wind coil is sized to fit within an aneurysm, fistula or vascular cavity; and
said primary wind coil being formed to have a secondary shape selected from the group consisting of cylindrical, conical, spherical and spheroidal shapes and combinations thereof.

10. The secondary wind coil of claim 9, wherein said exterior and interior non-circular primary wind coil cross-sectional shapes are double helix shapes.

11. The secondary wind coil of claim 9, wherein said exterior and corresponding interior non-circular primary wind coil cross-sectional shapes are selected from the group consisting of oval, oblong and generally triangular with rounded cornered shapes.

12. The secondary wind coil of claim 9, wherein said exterior and corresponding interior non-circular primary wind coil cross-sectional shapes are elongated along a second transverse axis that is transverse to said longitudinal axis, and wherein said second transverse axis and said interior non-circular primary wind coil cross-sectional shape precess along said longitudinal axis, said primary wind coil having a second plane of minimum bending force that correspondingly precesses along said primary wind coil longitudinal axis.

13. The secondary wind coil of claim 9, wherein said primary wind coil has an interior space along a longitudinal axis of the primary wind coil, and further comprising an axial strand of material extending through the interior space along the longitudinal axis of the primary wind coil.

14. The secondary wind coil of claim 9, wherein said primary wind coil has a variable bending moment in different planes of the primary wind coil, such that the plane of minimum bending force varies along the length of the primary wind coil.

* * * * *